(12) United States Patent
Bähler

(10) Patent No.: US 6,749,637 B1
(45) Date of Patent: Jun. 15, 2004

(54) ENDOPROSTHESIS FOR A SHOULDER JOINT

(76) Inventor: Andre Bähler, Kapfsteig 44, 8032 Zürich (CH)

( * ) Notice: Subject to any disclaimer, the term of this patent is extended or adjusted under 35 U.S.C. 154(b) by 0 days.

(21) Appl. No.: 10/088,630
(22) PCT Filed: Sep. 22, 2000
(86) PCT No.: PCT/CH00/00515
§ 371 (c)(1), (2), (4) Date: Mar. 20, 2002
(87) PCT Pub. No.: WO01/22905
PCT Pub. Date: Apr. 5, 2001

(30) Foreign Application Priority Data

Sep. 24, 1999 (CH) ............................................... 1743/99
Oct. 21, 1999 (DE) ...................................... 299 18 589 U

(51) Int. Cl.⁷ .................................................. A61F 2/40
(52) U.S. Cl. .................................. 623/19.14; 623/19.11
(58) Field of Search ........................... 623/19.11, 19.12, 623/19.13, 19.14

(56) References Cited

U.S. PATENT DOCUMENTS 3,815,157 A   6/1974   Skorecki et al.
4,011,603 A   3/1977   Steffee (List continued on next page.)

FOREIGN PATENT DOCUMENTS

| DE | 195 09 037 C1 | 9/1996 |
|---|---|---|
| DE | 19548154 | 6/1997 |
| DE | 196 16 059 A1 | 10/1997 |
| DE | 29918589 | 3/2000 |
| EP | 0 024 442 A1 | 8/1979 |
| EP | 0 208 578 A1 | 6/1986 |
| EP | 0 351 545 A1 | 6/1989 |
| EP | 0 532 440 A1 | 3/1993 |
| EP | 0 663 193 A1 | 12/1993 |
| EP | 0 586 335 A1 | 3/1994 |
| EP | 0 669 117 A1 | 8/1995 |
| EP | 0 679 375 | 11/1995 |
| EP | 0 712 617 A1 | 11/1995 |
| EP | 0 884 032 A1 | 6/1997 |
| EP | 0 850 609 | 12/1997 |
| EP | 0 903 128 | 3/1999 |
| EP | 0 963 741 A2 | 5/1999 |
| FR | 2 321 871 | 8/1975 |
| FR | 2 773 469 | 7/1999 |
| WO | WO 98/46172 | 10/1998 |
| WO | WO 99/34756 | 7/1999 |
| WO | WO 00/01327 | 1/2000 |
| WO | WO01/22905 | 9/2000 |

OTHER PUBLICATIONS

Search Reports for PCT/CH01/00676 dated Mar. 11, 2002 and Apr. 16, 2002.
Search Reports for PCT/CH01/00674 dated Feb. 26, 2002 and Jan. 16, 2003.
Search Report for PCT/CH01/00675 dated Feb. 26, 2002.

*Primary Examiner*—David J. Isabella
(74) *Attorney, Agent, or Firm*—Burns, Doane, Swecker & Mathis, L.L.P.

(57) ABSTRACT

The invention relates to an endoprosthesis for a shoulder joint comprising a rotating piece which is connected to a shaft part such that it can rotate around a first axis, and comprising an axial directional piece which is connected to said rotating piece such that it can rotate around a second axis. Both pivotal axes are perpendicular to one another and the second axis is perpendicular to the axis of the directional piece. The spherical cap is either placed directly on the directional piece, or an eccentric ring or an oblong hole ring which supports the spherical cap is provided between the spherical cap and directional piece. Two or more eccentric rings can also be provided. The spherical cap can comprise a centric or eccentric conical surface. The direction of the first axis can be selected in a relatively free manner.

40 Claims, 4 Drawing Sheets

U.S. PATENT DOCUMENTS

| | | |
|---|---|---|
| 4,318,190 A | 3/1982 | Cortesi |
| 4,528,702 A | 7/1985 | Frey |
| 5,314,485 A | 5/1994 | Judet |
| 5,458,649 A | 10/1995 | Spotorno et al. |
| 5,522,903 A | 6/1996 | Sokolow et al. |
| 5,702,457 A | 12/1997 | Walch et al. |
| 5,702,471 A | 12/1997 | Grundei et al. |
| 5,741,335 A | 4/1998 | Gerber et al. |
| 5,888,207 A | 3/1999 | Nieder et al. |
| 6,093,208 A | 7/2000 | Tian |
| 6,102,951 A | 8/2000 | Sutter et al. |
| 6,197,063 B1 | 3/2001 | Dews |
| 6,228,120 B1 | 5/2001 | Leonard et al. |

US 6,749,637 B1

ENDOPROSTHESIS FOR A SHOULDER JOINT

FIELD OF THE INVENTION

The invention relates to an endoprosthesis for a shoulder joint as generically defined by the preamble to claim 1.

PRIOR ART

From European Patent Disclosure EP 0 712 617, a shoulder joint prosthesis is known whose shaft part has an indentation with a hemispherical bottom in its metaphysial end, into which indentation a ball is introduced. This ball has a central continuous bore and a slot that communicates with the bore over its entire length and splits the ball ring, making it C-shaped. A stem connected to the cap is inserted into the bore. Grub screws are provided in the shaft part, in order to immobilize the ball in the indentation in a selectable angular position and to deform the ball ring and thereby firmly clamp the stem in it.

A disadvantage of this prosthesis is that the cap must be precisely placed in every direction before it can be fixed in this position. To that end, it must be held in this position by a surgeon while the grub screws are being tightened forcefully. Furthermore, the optimal position of the cap can be only approximated, since the spacing between the spherical cap axis and the shaft axis is constant. An alignment of the cap center in the anterior/posterior direction always necessarily involves a displacement in the cranial or caudal direction. Furthermore, the grub screws must be tightened before the prosthesis is inserted, because afterward they are no longer accessible. This requires multiple test manipulations of the arm being operated on and corrections to the cut face of the bone during the operation and makes a correction of the alignment after implantation has been completed impossible.

French Patent Disclosure FR 2 773 469 discloses a shoulder joint prosthesis with a shaft part and on it a pivotable adapter or directional piece, and the adapter has a ball cap. In this prosthesis, a hemispherical pit with a threaded bore on its bottom is provided on the metaphysial end of the shaft part. The pit and the threaded bore are aligned with a neck axis, whose angle to the shaft axis is selected in advance. Seated in the pit is a pivotable adapter, with a hemispherical surface, concentric with the hemispherical surface of the pit, on its humeral end. On its other end, the adapter has a conical surface, which is eccentric with regard to the center of the sphere common to the two spherical surfaces, on which conical surface the spherical cap is seated with a suitable conical indentation. The axis of this indentation is eccentric to the center point of the cap. The adapter has an axial bore with a hemispherical bottom. A screw with a ball head is introduced, with the shaft leading, into the bore, and the threaded portion of the shaft is punched through a conical bore in the hemispherical bottom of the adapter and screwed into the threaded bore in the shaft part. The centers of the spherical surfaces of the pit in the shaft part, the inner and outer hemispherical surface on the adapter, and the spherical surface of the screw head are located at a common central point, once the screw has been tightened. As a result, the adapter is pivotable relative to the shaft part in all directions and simultaneously rotatable. Pivoting the adapter causes its longitudinal axis to shift parallel to the desired neck axis direction, and rotating the adapter about its longitudinal axis and rotating the cap in a manner adapted to that rotation makes it possible to compensate for the deviation of the neck axis to be attained from the approximated neck axis. Once the optimal location of the adapter is definite, it can be fixed to the shaft part by tightening the screw.

In this prosthesis as well, the direction of the joint neck is adjustable infinitely variably, depending on the given conditions of the original joint. By adjusting the inclination and rotation relative to the shaft axis with the aid of a manipulation head, the neck axis is adjustable parallel to the optimal neck axis. This approximation can then be corrected infinitely variably afterward transversely to the direction of the axis with the cooperating eccentrically disposed conical surfaces on the adapter and the cap. The length of the joint neck is regulated by a set of caps of different thicknesses. In this way, a spherical cap can be made firm at any arbitrary site in any desired position, so that the site of the cap can be oriented optimally to the original conditions of the joint or the intended correction and the original center of rotation of the shoulder joint can be restored.

Since the success of a shoulder joint depends essentially on the restoration of the muscular equilibrium of the shoulder musculature, it is important that the original center of rotation of the shoulder joint be restorable by means of this individual placeability of the spherical cap. The closest possible spacing between the cut face of the bone and the artificial cap is also attainable, so that in every motion, the muscles are offered a continuous support point. It is also advantageous that the inclination and rotation of the adapter relative to the shaft part can be oriented to the cut face of the bone or to the desired orientation of the cap and can be fixed in that position even after the implantation of the shaft part, since the screw that fixes the adapter remains accessible from the side of the cap.

A disadvantage of this prosthesis, however, is that the spherical surfaces must be produced exactly concentrically, which is complicated and expensive. Ball joints furthermore offer a very small support face. In addition, the support face is reduced in size, in the region of the main direction for tightening the screw, by the conical bore in the spherical wall of the adapter. Ball joints in general have the disadvantage of not allowing a press fit in the sense of a conical clamping action. Therefore even after the operation is concluded, the fixation of this ball joint remains insecure.

Furthermore, the adapter must be placed correctly in every respect before it can be allowed to be fixed. In particular, a rotation about the directional axis, namely its own longitudinal axis, in order to rotate the eccentric cone into the desired position, is possible only if the angular position of the adapter is also unstable. Unintentional shifting of the adapter can occur upon removal of the manipulation head, insertion of the screw, tightening of the screw, and adjustment and placement of the spherical cap.

Finding the correct rotary position of the adapter in which the two eccentric conical surfaces of the adapter and spherical cap cooperate in such a way that the spherical cap comes to rest at the desired point is quite difficult. In practice, the eccentricity of the conical surface on the adapter is therefore oriented with the aid of a manipulation head in such a way that the cone axis is located as close as possible to the axis estimated to be optimal, and after that the cap is put in place. Upon alignment of the center of the cap in the anterior/posterior direction, however, there is necessarily also a shift in the cranial or caudal direction.

OBJECT OF THE INVENTION

It is therefore the object of the invention to propose an endoprosthesis for a shoulder joint in which the advantages of the prior art cited are preserved, while the aforementioned disadvantages of ball joints are avoided. In particular, the greatest possible forces of friction should be attained between the individual parts that are displaceable and rotatable counter to one another. Moreover, it should be possible to define the direction and position of the joint axis independently of one another. Compared to the prior art, the calibration of direction and location of the spherical cap axis should be simplified. The sensitivity of the settings of the axial direction, in terms of inclination and rotation, to unintended changes in the inclination position or rotation position should be minimized as much as possible by adjustment of the other setting. Also, the direction of the axis should have the slightest possibly vulnerability to influence from a change in the location of the spherical cap axis relative to the location of the longitudinal axis of the adapter or the directional piece as possible.

DESCRIPTION OF THE INVENTION

This object is attained by disposing a rotating piece between the shaft part and the directional piece, the rotating piece being rotatable relative to the shaft part and a first axis, and the directional piece is supported rotatably relative to the rotating piece about a second axis, and this second axis extends transversely to the first axis and transversely to the directional axis; contact faces between the shaft part and the rotating piece, on the one hand, and between the rotating piece and the directional piece on the other each allow only a relative motion between the shaft part and rotating piece, and the rotating piece and directional piece, respectively, about the respective common first and second axis, as a center of rotation.

As a result of this separation of the pivoting motion of the directional piece into two pivoting motions about two axes that cross one another, the full range of motion that a ball joint offers is preserved, yet in comparison to a ball joint the risk of unintended change of a pivoted position relative to the one axis is markedly reduced by a pivoting about the other axis. The articulation and friction faces between the shaft part, rotating piece and directional piece are not spherical surfaces but rather surfaces of axial bodies of rotation, such as a cylinder, torus, or cone, to name only the simplest ones, whose surfaces are simpler to produce precisely. The contact faces can therefore be embodied with a larger area than spherical surfaces. A press fit is also possible, because conical portions can be provided in the articulation face. The alignment of the first axis around which the rotation piece is rotatable relative to the shaft part can be parallel to a neck axis of the natural joint. It is also possible to have the first axis approximately perpendicular to the neck axis or to the directional axis, and the second axis approximately perpendicular to these two axes. It is also possible to align the first axis with a directional deviation from the direction of the neck axis. This deviation is advantageously less than 60 degrees and preferably less than 50 degrees. Then the second axis is placed crossing the first. As a consequence, both the rotational position and the inclination position can be set. Advantageously, the direction of the first axis is selected to be approximately parallel to or even better in the same plane as that passing through the shaft axis and neck axis. Upon pivoting or rotation of a part of the prosthesis about an axis that is parallel to or located in this plane, the inclination is not adjusted. Only the alignment of the second axis that crosses the first axis is adjusted. As a result, the adjusting direction, dictated by the second axis, can be set. In particular, an alignment of the first axis parallel to the neck axis is expedient.

If the first axis intersects the neck axis, or if the two coincide, then pivoting of the rotating piece about this first axis causes practically no elongation or shortening of the joint neck.

Advantageously, at least one eccentric ring or one oblong slot ring is provided between the directional piece and the spherical cap. This ring makes it possible to vary and define the location of the cap, or the spacing between the directional piece and the center of the cap. This makes it possible to choose the direction and amount of the spacing between the directional piece and the spherical cap axis or the center of the spherical cap. In this way, a displacement of the second axis resulting from pivoting about the first axis can also be compensated for. It is therefore not necessary for the first and second axes to intersect at a point.

In a simplified embodiment, the cap can be placed directly on the directional piece. The indentation with which it is placed on the directional piece can be machined into the cap centrally or eccentrically. Nor does the cap have to have a spherical surface; instead, it can have an embodiment that differs from this idealized articulation face.

Expediently, the directional piece has an external cylindrical or conical surface, whose center of rotation is the longitudinal axis of the directional piece, that is, the directional axis. The spherical cap, eccentric ring or oblong slot ring can be placed on this surface. The conical surface is preferred, on which these parts can be fixed by being pressed onto the directional piece. For the oblong slot ring, which in any case requires a fixation device, such as grub screws, the surface can readily be cylindrical. Cylindrical surfaces in combination with fixation devices, both in the case of an oblong slot ring and in the case of an eccentric ring, make it possible to choose the spacing between this ring and the shaft head, and accordingly the spacing between the center of the spherical cap placed on it on the one hand and the shaft axis on the other.

The alignment of the first axis preferably corresponds to the alignment of a preselected neck axis. As a result, the rotating piece is supported in the shaft part rotatably about the neck axis and can be secured to the shaft part in a manner fixed against relative rotation by very simple means. By adjustment of the directional piece about the second axis relative to the rotating piece, forces which tend to pivot the rotating piece about the first axis need hardly be expected, at least in a narrower region around the middle position, since these two axes and pivoting directions are essentially perpendicular to one another. Since the first axis extends approximately parallel to the directional axis, a fundamentally different manipulation is required for rotation about this first axis compared to that for pivoting about the second axis that is perpendicular to the directional axis.

Advantageously, the rotating piece has a concave rotational body surface oriented toward the directional piece, with the second axis as its center of rotation. Alternatively, however, the rotating piece has a convex rotational body surface oriented toward the directional piece, with the second axis as its center of rotation. In particular, a cylindrical, toroid or conical surface is conceivable, but also more-complicated rotational body surfaces, for instance with steep conical side faces or faces curved in multiple directions, and actual hinge joints with axle bolts placed in them are equally conceivable.

Although the two axes need not intersect, nevertheless in one embodiment the first axis intersects the second axis at a central point. As a result, it is possible to fix the two pivoting motions in common, using a single common fixation device.

To that end, both this fixation device, which is preferably a screw that can be screwed into a threaded bore in the shaft part, and the directional piece must have contact faces that rest on spherical surfaces whose centers, in the screwed-together state, coincide with the point of intersection of the two axes, that is, the central point.

Advantageously, there is a recess with a side wall in the shaft part, which side wall is equivalent to a surface of rotation about the first axis or the neck axis. In it, a rotating piece with an outline corresponding to the side wall is supported rotatably about the first axis, and this rotating piece has an articulation face for the directional piece, in the form of a surface of rotation about the second axis. The side wall can be cylindrical or conical or can be provided with a thread. In each case, the rotating piece can be rotated by at least 360 degrees prior to the fixation. Upon fixation, in the case of the conical side wall, a conical clamping to the side wall results, while in the case of the cylindrical side wall, the pressure is exerted via the bottom face of the indentation or of the rotating piece. In the case of a thread, the pressure is exerted over large areas, namely the flanks of the thread.

The directional piece has a shape that is complimentary to the articulation face, toward the directional piece, of the rotating piece and also has an axial conical surface onto which a conical surface of the spherical cap or of an eccentric ring can be slipped. The articulation faces between the directional piece and the rotating piece need not meet over a large area but instead can rest on one another merely linearly or even at a point. For fastening the directional piece to the shaft part, a threaded bore is advantageously provided in the shaft part. The directional piece has an internal bore, in which there is space for the head of a screw, as well as a bore for the screw shaft. With the screw, the directional piece can be screwed into the threaded bore, through a bore in the rotating piece. The bore in the directional piece for the screw shaft is embodied as a slot, which allows a range of motion of the screw shaft of 30 degrees, and whose width is adapted to the diameter of the screw shaft, in particular to the diameter of a threadless part thereof that cooperates with the bore, in order to prevent lateral shifting of the directional piece relative to the rotating piece.

In another embodiment, the two independent rotary motions about the first axis and the second axis are also fixable individually. This makes it easier to lock or fix the individual pivoting motions. As a result, first the rotation of the directional axis relative to the shaft axis can for instance be defined and fixed, and then in a second step the inclination can be determined and fixed.

Where given conditions allow, the spherical cap can have an inner conical surface that instead of being centrally disposed is eccentric relative to the spherical cap, and this inner conical surface can be slipped onto the outer conical surface of the directional piece or of the eccentric ring. As a result, the spacing and direction between the center of the cap and the longitudinal axis of the directional piece can be set. The eccentricity of both the inner conical surface in the cap and the outer conical surface on the eccentric ring is not visible, however, because it is concealed by the cap. This makes the targeted setting of the direction and distance more difficult. For this reason, two eccentric rings that can be put together via conical surfaces are therefore disposed between the spherical cap and the directional piece. They allow visual checking of the location of the cone outlines relative to one another and relative to the outline of the cut face of the bone, so that the eccentric rings can be placed in the center of the outline, so that after that a cap with a central conical surface can be placed on the second eccentric ring.

Advantageously, however, a manipulation head is used instead of a second eccentric ring. The manipulation head has an inner conical surface, disposed eccentrically relative to the spherical cap axis, which can be slipped onto the outer conical surface of the eccentric ring, and whose eccentricity is equivalent to the eccentricity of the inner conical surface of the spherical cap. Furthermore, it is shaped annularly in such a way that the eccentric ring is visible and adjustable through the eccentric annular opening of the manipulation head. In setting the eccentric ring, this makes visual comparison possible between the edge of the manipulation head and the edge of the cut plane of the bone. Because the eccentricities of the cap and manipulation head match, the optimal rotary position of the eccentric ring can easily be fixed by this comparison and the eccentric ring can be firmly hammered or pressed onto the directional piece, and the cap can be placed at the same as the manipulation head, in the same alignment. After that, with an optimally oriented directional piece and eccentric ring, finding the optimal rotary position of the cap is easy.

Alternatively to an eccentric ring between the directional piece and the cap, it is also possible to provide an eccentric part between the rotating piece and the shaft part. The fixation of the eccentric part to the shaft part can be done for instance with a ring screw. The rotating piece and directional piece then need to be secured to the eccentric part.

As an alternative to the double eccentric ring, an oblong slot ring can be provided, which has an oblong slot with which it can be slipped onto the directional piece. The ring has a fixation device, with which it is fixable on the directional piece in a selectable displacement and rotary position relative to the directional piece. The use of an oblong slot ring between the directional piece and the spherical cap is independent of the pivoting device on the shaft part. Accordingly, an oblong slot ring can also be used in a prosthesis in accordance with the known prior art.

In a version of the directional piece that is advantageous for production, its length is located inside a roller or cylinder part having the radius of the convex articulation face. This makes it possible to produce the directional piece from a rolled piece with that radius, by machining the connecting part to the joint head with the internal bore out of the rolled part using metal-cutting means.

In an alternative version to the above, with a screw screwed into the shaft part, a bore that is concentric with the articulation face about the second axis is provided in the rotating piece. This body or head part is connected to a screw shaft, and the wall between the bore and the articulation face has a slot extending transversely to the second axis, through which slot the screw shaft passes. The directional piece has an articulation shim and a pressure shim, and the articulation shim has a bore for the screw shaft and an articulation face corresponding to the articulation face of the rotating piece, and on the opposite side also has a pressure face cooperating with the pressure shim. The pressure shim is connected to the screw shaft. The connection between the pressure shim and the screw shaft assures that by rotation of the pressure body or of the screw shaft, a relative rotation between the screw shaft and the cylindrical body and/or the pressure body results and thereby the distance between the cylindrical body and the pressure shim is varied. To that end, either in the cylindrical body or in the pressure body, or in both, a female thread is provided, which cooperates with a male thread on the screw shaft. By this means the directional piece and the rotating piece can be fixed against one another. The rotating piece is therefore in turn advantageously fixable to the shaft part with a ring that can be screwed onto or into the shaft part, independently of the fixation of the directional piece to the rotating piece.

Advantageously, in such an endoprosthesis for a shoulder joint, at least two of the following parts are put together prior to the implantation of the prosthesis and are available secured at least temporarily to one another: shaft part, rotating piece including an optional head piece, directional piece including an optional articulation shim and pressure shim, and screw, as well as an optional eccentric shim or oblong slot shim. These parts are secured against falling out, for instance with union rings or tongues. This has the advantage that the surgeon need not take small parts, which are hard to manipulate, into his fingers. An expedient combination from among the series of possibilities is to provide the shaft part with the rotating piece secured on it and to provide the directional piece separately, if need be composed of the articulation shim and pressure shim, with a screw inserted or a screw shaft. The rotating piece can also be combined with the directional piece, or all the parts can be temporarily put together.

The cooperating concave and convex contact faces between the rotating piece and the directional piece, between the directional piece and the screw, and between the directional piece and the articulation shim can correspond to one another in geometry and size. However, they can also correspond merely in such a way that a linear contact takes place between the contact faces. To that end, the articulation face on the rotating piece is for instance embodied as a groove, with two flat faces at an angle to one another. The bore in the directional piece into which the screw is inserted correspondingly has a conical bore, rather than a hemispherical hollow, or has one or more circular edges along approximately the same geometric spherical surface. The articulation shim in turn is equipped, like the rotating piece, with for instance two flat faces at an angle to one another. The contact faces can also have edges or spurs that can be pressed into the counterpart face when the screw is tightened. The linear contact has the advantage over area contact that the contact faces are pressed against one another, causing deformation of material, and as a result the connection once the screw is tightened is quite stable. Embodying the concave contact faces in such a way that they touch the convex contact face only along a line furthermore has the advantage that the concave contact faces can be produced very simply and economically.

BRIEF DESCRIPTION OF THE DRAWINGS

The invention will be described in further detail below, in conjunction with the examples schematically shown in the drawings. Shown are.

DESCRIPTION OF THE EXEMPLARY EMBODIMENTS

Figure 1:
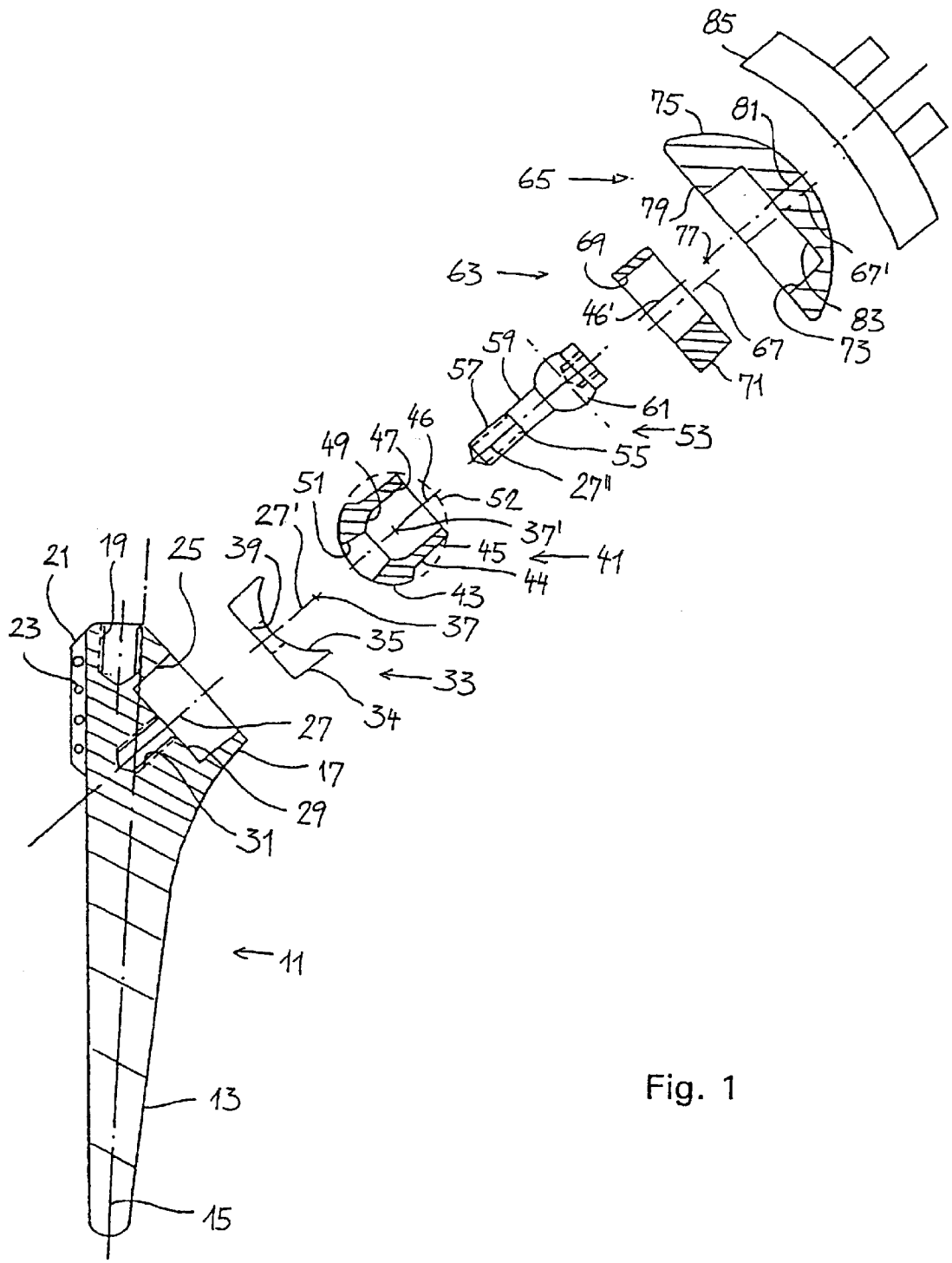
FIG. 1: an exploded view of a first exemplary embodiment, with some parts shown in section.

The first exemplary embodiment in FIGS. 1–5 has a shaft part 11, with a shaft stem 13 along a shaft axis 15 and with a shaft head 17. On the shaft head 17, a device 19 for introducing the shaft stem 13 into the bone is provided. This device also serves to remove the shaft stem from the bone. A rib 21 with bores 23 is also provided on the shaft head 17. Soft parts can be tacked to this rib 21 or to the bores 23. A concave, frustoconical articulation face 25 is also provided on the shaft head 17, and its axis 27 is parallel to the neck axis of the natural joint (not shown in the FIG. 1 view), in this case at an angle of 135 degrees to the shaft axis 15, and will hereinafter be called the first axis. Axially to this first axis 27, a bore 31 with a female thread is provided in the bottom 29 of the articulation face 25.

A rotating piece 33 (see also FIG. 5) can be inserted into the concave indentation in the articulation face 25 on the shaft part 11. The rotating piece 33 is a conical disk, or truncated cone, with an inclination of the conical jacket 34 that corresponds to the inclination of the conical jacket of the articulation face 25. On the side of the base of the truncated cone, the rotating piece 33 has a cylindrical recess 35, with a second axis 37 transverse to a first axis 27. Axially to the first axis 27, a bore 39 is provided in the rotating piece 33.

The directional piece 41 (see also FIG. 4) fits into the recess 35. It has a cylindrical articulation face 43, which is curved to complement the cylindrical surface 35 of the recess. The axes of the surfaces complementary to one another coincide in the assembled state, and the axis of the articulation face 43 on the directional piece 41 is therefore identified by reference numeral 37'. A connecting part 44 with a frustoconical jacket or conical face 45 is also provided on the directional piece 41. The axis 46 of the connecting part 44 and of the conical face 45 is perpendicular to the axis 37' of the articulation face 43. The joint head of the prosthesis can be slipped onto this connecting part 44 from the side remote from the articulation face 43. The directional piece 41 has an axial bore 47 with a hemispherical bottom 49, beginning on the side toward the joint head, and also has a conical oblong slot bore 51 through the articulation face 43. The longitudinal direction of the oblong slot bore 51 is oriented perpendicular to the axial direction of the articulation face 43; the conical embodiment of the oblong slot 51 exists solely on its ends.

The shaft part 11, rotating piece 33 and directional piece 41 can be put together with the complementary fitting shapes, that is, the articulation face 25 on the shaft part and the truncated cone with the conical jacket 34 on the rotating piece 33, as well as a cylindrical recessed face 35 on the rotating piece and an articulation face 43 on the directional piece 41 on the other, and can be screwed together with a screw 53. The screw 53 has a shaft 55 with a threaded portion 57 and a smooth shaft part 59, as well as a spherical screw head 61. The radius of the sphere of the shaft head is equivalent to the radius of the spherical bore bottom 49 of the directional piece 41. The shaft head can also have a shape other than the spherical, as shown in FIG. 1a. The directional piece 41 is machined out of a rolled piece 52. The radius of the rolled piece is the radius of the articulation face 43.

If the shaft part 11 and the directional piece 41 are to be put together, then first the rotating piece 33, with the cylindrical recess outward, is inserted into the frustoconical, indented articulation face 25 in the shaft part 11, and then the directional piece 41 is inserted with its cylindrical articulation face 43 into the cylindrical surface 35 of the recess. Next, the screw 53 is introduced, with the shaft 55 leading, into the bore 47, and the screw shaft 55 is forced through the oblong slot bore 51 in the directional piece and through the bore 39 in the rotating piece 33 and screwed into the thread in the bore 31 in the shaft part 11. Once the screw has been tightened firmly, the axes 37 and 37' coincide, and the center point of the spherical shaft head 61 is located at the point where the axes 37, 37' intersect the first axis 27.

If the screw 53 is not tightened firmly, then on the one hand the rotating piece 33 is rotatable about the first axis 27 in the shaft part, and as a result the direction of the second axis 37 can be chosen, and on the other hand, the directional piece 41 is pivotable about the second axis 37 in the rotating piece 33. By superposition of these two rotary and pivoting motions, the directional axis 46 can be adjusted in all directions, at a selectable angle to the preselected neck axis, which in this exemplary embodiment is equivalent to the first axis 27. The angle between the first axis 27 and the directional axis 46 can be selected to be between 0 and about 30 degrees. The angle with respect to the rotation of the rotating piece about the first axis 27 can be selected as between 0 and 360 degrees.

In order that the surgeon will have the most conveniently handled parts in his hand, small parts are expediently brought together and joined together before being implanted; for instance, the rotating piece 33 can be left in the shaft part 11 and fixed or secured therein. The screw 53 can be inserted into the directional piece 41 and secured therein. For the sake of preparation, the screw 53, directional piece 41 and rotating piece 33 can also be put together and temporarily joined to one another. Further possible ways of reducing the number of parts to be assembled during the operation and of combining the small parts are for the directional piece 41 and the rotating piece 33 to be put together beforehand, or for the directional piece 41, rotating piece 33 and shaft part 11 to be put together, with or without the screw 53. The screw 53 can be loose or can be tightened in a temporary position of the directional piece 41. Analogous combinations of parts are appropriate in the other exemplary embodiments as well.

The head of the joint prosthesis can be slipped onto the directional piece 41, which is oriented in the optimal joint neck direction and is fixed in this position by the screw 53. The head of the joint prosthesis, in the exemplary embodiment of FIG. 1, comprises an eccentric ring 63 and a spherical cap 65, with a radius corresponding approximately to the original articulation face of the shoulder joint to be replaced. The eccentric ring 63 has two frustoconical jacket faces, oriented in the same direction, with spaced-apart, parallel axes 46' and 67 (see also FIG. 3). This eccentric ring 63 has an inner conical face 69, disposed centrally about the axis 46' and adapted to the conical face 45 of the directional piece 41, and an outer conical face 71, with the eccentric axis 67 as the center of rotation. The outer conical face 71 of the eccentric ring 63 is adapted to the conical face 73 in the spherical cap 65.

The spherical cap 65 is advantageously a spherical segment similar to the removed bone segment of the joint ball. The articulation surface 75 of the cap 65, for an idealized cap, is located on a radius about its center point 77 of the sphere. The cap 65 has a flat underside 79 opposite the spherical surface 75. The plane of the underside 79 geometrically intersects the theoretical spherical surface along a circle. A spherical cap axis 81 is determined by the center point of this circle and the center point 77 of the sphere. Eccentrically to the spherical cap axis 81, a conical indentation 83 is provided in the underside 79; its conical wall 73, embodied axially around the eccentric axis 67', and the depth thereof are adapted to the mass of the outer conical face 71 of the eccentric ring 63. The spherical surface 75 of the cap 65 is intended to cooperate with the natural joint face of the glenoid, or with an implanted glenoid part 85.

The joint head is placed on the directional piece 41, which is done by pressing the inner conical face 69 of the eccentric ring 63 onto the conical face 45 of the connecting part 44, and the cap is pressed with the indentation 83 onto the outer conical face 71 of the eccentric ring. In the process, the axes 46 and 46' coincide, as do the eccentric axes 67 and 67'. By rotating the eccentric ring about the directional axis 46 and by rotating the cap about the eccentric axis 67, the direction and spacing between the axes 46, 46' and 67/67' can be added to the direction and spacing between the axes 67, 67' and 81 as vectors. On the condition that the axis spacings are equal, the spherical cap axis 81 can be disposed at a selectable spacing from the longitudinal axis 46 of the directional piece 41 that is between 0 and the total of these axis spacings. The spherical cap axis can furthermore be put into an arbitrary rotary position between 0 and 360 degrees about the directional axis 46, without rotating the directional piece 41. As a result, after the fixation of the direction of the directional axis 46, the spherical cap axis 81 can be oriented exactly through the original joint ball center point.

If the osteotomy is performed such that the bone cut is made along the edge of the joint ball, then the underside 79 of the cap can be aligned parallel relative to the cut plane of the bone, by orienting the directional piece 41 perpendicular to the cut plane of the bone. The location of the spherical cap axis 81 can subsequently be ascertained from the outline of the bone section. The position of the spherical center point must consequently still be set in a known manner by means of a set of spherical caps 65, differing in terms of the cap height, on the basis of the muscle tension.

Figure 1A:
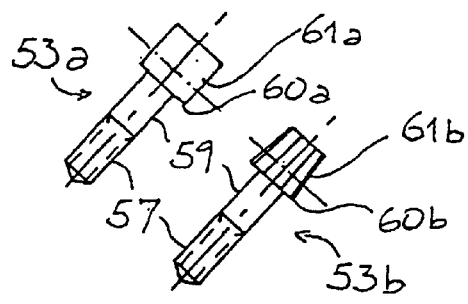
FIG. 1a: two variants of the screw 53 of FIG. 1.

FIG. 1a shows two variants 53a and 53b of the screw 53 of FIG. 1. Once again, they have a shaft part 57 with a thread and a smooth shaft part 59, but the shaft head is of cylindrical shape 61a, or frustoconical or prismatic shape 61b. Thanks to this non-spherical shape of the shaft head 61a, b, the result is an annular, virtually linear contact-pressure face between the shaft head 61a, b and the spherical recess 49 in the directional piece 41. The contact-pressure edge 60a, b of the shaft head 61a, b can be rounded by chamfer removal or sharp-edged. With this contact-pressure edge 60a, b, the directional piece can be held against the rotating piece 33 without impairing the free pivotability about the center 37' of the sphere. In every pivoted position of the directional piece 41, the edge 60a, b rests along a circle on the spherical recess 49. Upon tightening of the screw 53a, b, however, this contact-pressure edge 60a, b is pressed into the spherical recess 49, so that the fixation of the directional piece is accomplished more reliably than in the event of an aerial contact of a spherical shaft head 61.

Figure 1B:
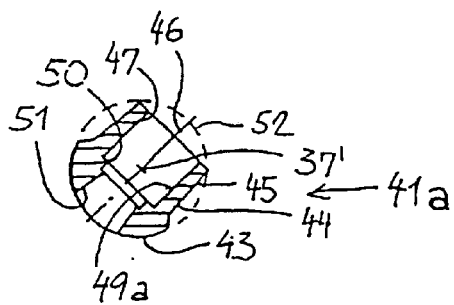
FIG. 1b: a variant of the directional piece 41 of FIG. 1.

Conversely, with a correspondingly similar effect, it is also possible to shape the recess 49 with a cylindrical or conical jacket-shaped inner face 49a, which has an annular contact-pressure edge 50 in one end face of the recess 49 of the directional piece. One such directional piece 41a is shown in FIG. 1b. This contact-pressure edge 50 cooperates with a spherical shaft head 61. The contact-pressure edges 50 and 60 can also be embodied as double, triple or multiple. To that end, they must merely be located on a theoretical spherical surface about the center point 37' of the sphere. Advantageous, they are located in a plane that is perpendicular to the axis of rotation of the screw. If there are many contact-pressure edges 50 or 60 on the directional piece 41a or on the screw 53a, b, then both the recess 49a and the shaft head 61a, b can deviate from a purely spherical shape and can have contact-pressure edges 50, 60.

Figure 2:
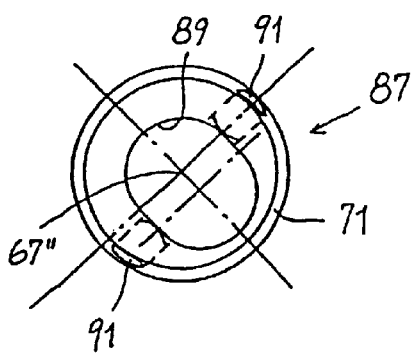
FIG. 2: an elevated view of an oblong slot ring.

In FIG. 2, an oblong slot ring 87 is shown. The oblong slot ring 87 can be used as an alternative to the eccentric ring 63. If an oblong slot ring 87 is used, it is unnecessary to disposed the conical indentation 83 eccentrically in the underside 79 of the cap. On the contrary, the indentation is advantageously disposed centrally. Analogously to the eccentric ring 63, the oblong slot ring 87 has an outer conical face 71 corresponding to the conical indentation 83 in the underside 79 of the cap 65. If the conical indentation 83 is expediently disposed centrally in the underside 79 of the cap, then the conical face can also be shaped as other than a strictly frustoconical jacket face, for example as a truncated pyramid. The oblong slot ring has an oblong slot 89, parallel to the eccentric axis 67", the length of the oblong slot extending transversely to the eccentric axis 67'. The oblong slot 87 has two semicylindrical or two semifrustoconical walls with two flat connecting faces. The center of the one wall, which is semicircular, is located on the eccentric axis 67", while the center of the other wall is at a selected spacing from it.

The oblong slot can be conical, if the directional piece 41 to be thrust into the oblong slot has a cone 45. However, the directional piece 41 can also have a cylindrical connecting part 44. That, however, requires fixation means in the eccentric ring 63 or in the oblong slot ring 87. Fixation means, in particular two grub screws 91, are disposed in the oblong slot ring 87. One of them is oriented perpendicular to the length of the oblong slot, toward the center of the one semicircular wall, and the other is oriented toward the center of the other wall. As a result, a connecting part 44 of the directional piece 41 that is introduced into the oblong slot 89 can be fixed in a selectable rotary position and displacement position in the oblong slot.

Figure 3:
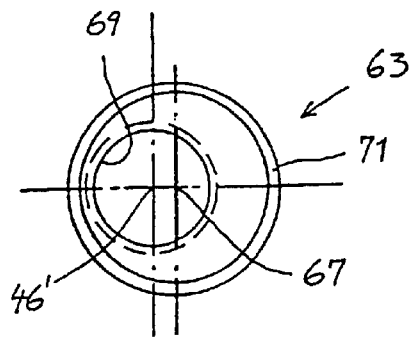
FIG. 3: an elevated view of an eccentric ring.
Figure 4:
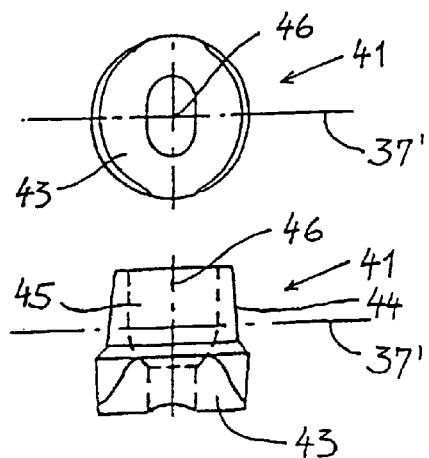
FIG. 4: a view from below and from the side of the directional piece in the example shown in FIG. 1.
Figure 5:
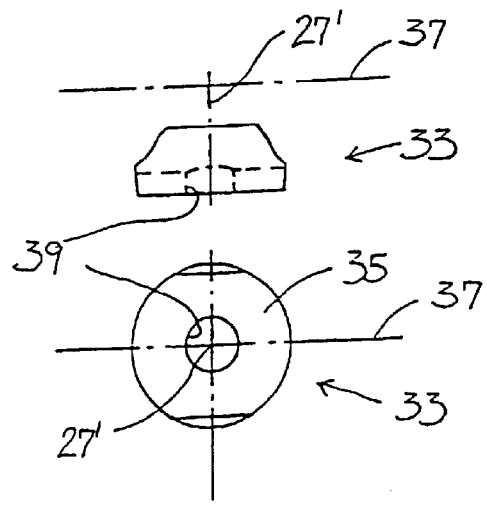
FIG. 5: a side view and elevation view of the rotating piece of the example shown in FIG. 1.
Figure 6:
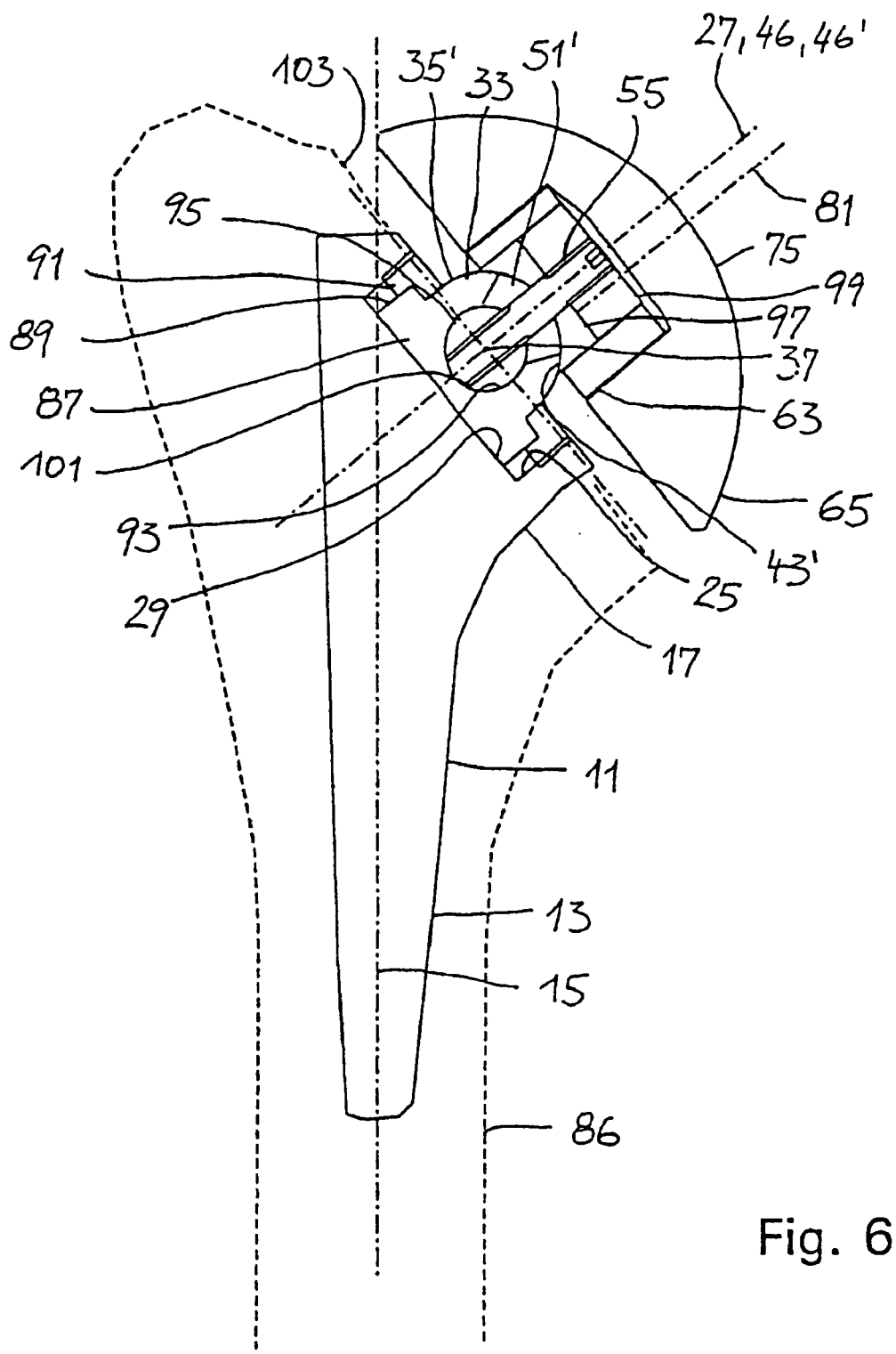
FIG. 6: a schematic section through a second exemplary embodiment, in the assembled state.
Figure 7:
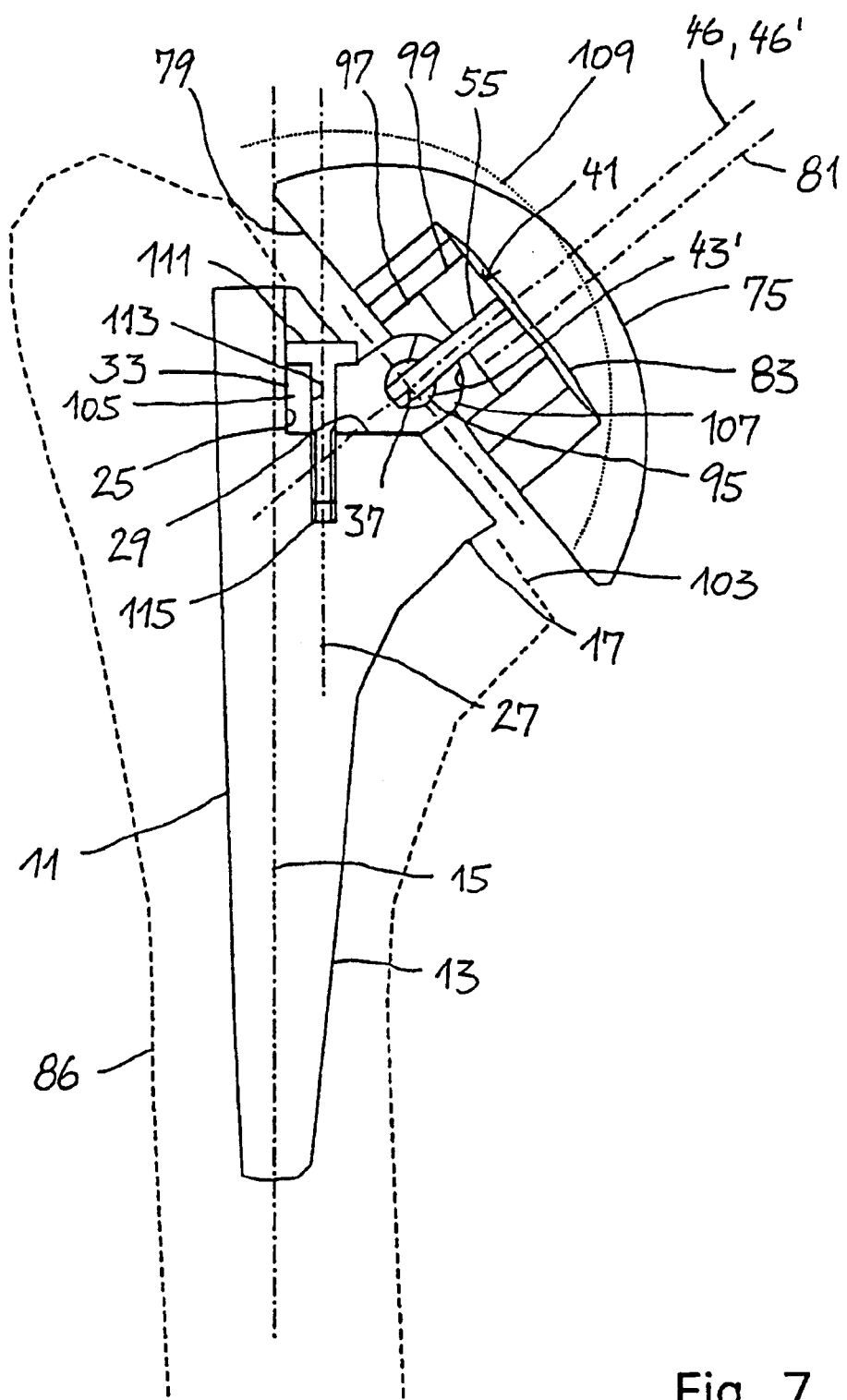
FIG. 7: a schematic section through a third exemplary embodiment, showing the humerus, with flat contact faces on the articulation shim.

FIGS. 3–5 have been described above in conjunction with the exemplary embodiment of FIG. 1. In FIGS. 6 and 7, two further exemplary embodiments are shown. The corresponding elements are identified by the same reference numerals, even if the parts sometimes have shapes that deviate substantially.

In the schematic section of FIG. 6, a second exemplary embodiment is shown, in which, as in the first example, the first axis 27 corresponds to the middle neck axis, and the first axis 27 and the second axis 37 intersect at a point, which after the implantation of the shaft in the humerus bone 86 is located as nearly as possible in the cut plane 103 of the severed joint ball of the bone. In this exemplary embodiment, however, the rotating piece 33 has a convex cylindrical face 35. Also, the rotating piece 33 is fixable to the shaft part 11 independently of the fixation of the tilting motion of the directional piece 41 relative to the rotating piece 33. To that end, the following construction is provided:

In the shaft part 11, and in particular in the shaft head 17, a cylindrical indentation 25, whose cylinder axis 27, that is, the first axis, is oriented somewhat along the natural neck axis. This indentation 25 is provided with a thread. In this indentation 25, the rotating piece 33 is disposed rotatably about the first axis 27. The rotating piece 33 has a base 87 with a circular edge 89, and this edge 89 protrudes laterally beyond a semicylindrical bulge. This bulge is the articulation face 35' for the directional piece 41. This edge 89 cooperates with a ring screw 91, screwed into the thread in the indentation 25, in such a way that by tightening the ring screw 91, the edge 89 is pressed against the bottom 29 of the indentation 25. As a result, the rotating piece 33 is fixed in the indentation 25. The axis 37 of the semicylindrical bulge 35, that is, the second axis, extends perpendicular through the first axis 27. A bore 93 is provided in the rotating piece 33, concentrically with the bulging face 35. A cylindrical body 95 is placed in the bore 93 and fills the diameter of the bore. This body or head part 95 is rotatable in the bore about the axis 37. A screw shaft 55 is connected to the head part 95. The screw shaft is perpendicular to the second axis 37. In FIG. 6, the screw shaft 55 is even oriented along the middle neck axis. The screw shaft 55 punches through the wall between the bore 93 and the articulation face 35'. To that end, a conical oblong slot bore 51' is provided in this wall on the rotating piece 33. The length of the oblong slot bore 51' is oriented perpendicular to the axial direction of the articulation face 35', and the oblong slot 51' is embodied conically only on its ends. The oblong slot allows a rotation of the head part 95 together with the screw shaft 55 about the second axis 37.

An articulation shim 97 and a pressure shim 99 that takes over the task of the connecting part 44 are slipped onto the screw shaft 55. The articulation shim 97 and the pressure shim 99 together form the directional piece 41 that is pivotable about both the first and the second axis. The articulation shim 97 has a circular outline with the axis 46 and has a concave cylindrical face 43' on one side, corresponding to the articulation face 35' on the rotating piece, and on the opposite face it has a pressure face, against which the pressure shim 99 can press over a large area. A bore through which the screw shaft 55 fits is embodied axially in the articulation shim 97. The pressure shim 99 has a circular outline with the axis 46. A threaded bore is embodied axially, and with it the pressure shim 99 can be screwed onto the screw shaft 55. Alternatively, the pressure shim 99 can be solidly connected to the screw shaft 55, but that requires a threaded connection between the screw shaft and the head part 95.

This threaded connection between the head part 95 and the screw shaft 55 is, however, also advantageous in other ways, because it permits an initial fixation of the head part 95 in the rotating piece 33, before the directional piece 41 is disposed on the screw shaft 55. By tightening the screw shaft in the head part 95, the head part can be clamped to the rotating piece in a simple way. However, if a pointed tip 101 is formed on the screw shaft 55 toward the shaft part or the head part, then when the screw begins to be tightened this pointed tip drills into the rotating piece 33, so that the rotatability of the directional piece about the second axis 37 is securely prevented.

Alternatively, the rotating piece 33 can be embodied in such a way that the bore 93 is opened toward the shaft part 11 and surrounds the head part 95 only on the side toward the directional piece 41 but leaves it free toward the bottom 29 of the indentation 25 in the shaft part 11. In that case, the head part 95 is then seated in a slot, embodied parallel to the second axis 37, having the same width and height as the head piece 95 and with a semicylindrical slot bottom. This makes it possible to press the pointed tip of the screw shaft into the bottom 29. To that end, the bottom in this region can have a concave spherical surface, with the center at the point of intersection of the first and second axes, so that the pointed tip 101 punches into the bottom 29 perpendicular to the surface thereof. This also prevents the unintended rotation of the rotating piece about the first axis.

By screwing the connecting part 99 onto the screw shaft 55, or by firmly screwing the screw shaft, secured to the connecting part, into the head part 95, the head part 95 and articulation shim 97 are in each case pulled together. As a result, the directional piece 41 can be fixed to the rotating piece 33 in any pivoted position.

The pressure shim 99 has an outer conical face 45, onto which an eccentric ring 63 is slipped. The spherical cap 65 is seated on the eccentric ring 63. Because of the eccentricity of the eccentric axes 46', 67 and of the axes 67' and 81 of the conical indentation 83 on the cap 65 and on the spherical cap 65, the spherical cap axis 81 can be disposed in a selectable direction and at a selectable spacing relative to the directional axis 46 (the eccentric axes 67, 67' are not shown). The directional axis 46 is pivotable relative to the first axis 27 (or to the shaft axis 15) in a selectable direction and by a selectable angle. Alternatively, the eccentric ring can also be omitted, and the spherical cap can be placed directly onto the conical surface of the directional piece.

Thanks to this adjustability of the axes, it is possible in a first step to adjust the directional axis 46 perpendicular to the cut face 103 of the bone and to fix the directional piece and the rotating piece in this position. In a second step, the location of the spherical cap axis 81 relative to the directional axis 46 can then be adapted to the outline of the cut bone, and the cap 65 can be hammered firmly onto the directional piece 41.

The third exemplary embodiment of FIG. 7, finally, makes it clear that the first and second axes need not necessarily intersect at a common pivot point in or near the cut plane 103 of the bone. The axes 27 and 37 can extend at right angles or obliquely to one another and can be spaced apart from one another. In the third exemplary embodiment, the first axis 27 is not aligned with the natural neck axis but instead is aligned parallel to the shaft axis 15. As a result, the recess 25 in the shaft part 11, in which recess the rotating piece 33 is supported and fixable, is oriented orthogonally to the shaft axis 15. The rotating piece 33 has an articulation part 105 toward the shaft and an articulation part 107 toward the directional piece. The articulation part 107 toward the directional piece is embodied analogously to the cylindrical bulge 35' of the second exemplary embodiment and is provided with a convex articulation face 35, but it could also have a concave articulation face 35, analogously to the first exemplary embodiment. Once again, a cylindrical head part 95 is disposed in a cylindrical bore 93 that is concentric with the cylindrical articulation face 35'. Through an oblong slot bore 51' in the wall with the articulation face 35', the screw shaft 55 is screwed into the head part 95. As a result, the screw shaft 55 has a pivoting freedom corresponding to the length of the oblong slot bore 51'. As in the second exemplary embodiment, an articulation shim 97 and a pressure shim 99 are disposed on the screw shaft. The pressure shim 99 together with the articulation shim 97 forms the directional piece 41.

Alternatively, the directional piece can be formed by the pressure shim 99 alone. In that case, the articulation shim 97 is expediently embodied with a smaller diameter than the pressure shim 99. Two eccentric rings 63, 64 are seated on the directional piece 41. The location of the spherical cap axis 81 can be set using the two eccentric rings. The cap 65 therefore has a recess 73 in its underside 79, which recess cooperates with the second eccentric ring 64 and is located centrally on the spherical cap axis 81. By rotating the eccentric rings 63, 64, the outer conical face 71' of the outer eccentric ring 64 can be disposed in such a way relative to the outline of the cut bone that the cap 65, after the eccentric ring 64 has been put in place, is seated optimally relative to the location of the original articulation face axis.

The rotary position is fixed by tightening the screw 111. The screw 111 is axial to the first axis 27 and forms the pivot axis for the rotating piece 33 relative to the shaft part 11. To that end, in its articulation part 105 toward the shaft, the rotating piece has an axial bore 113, through which the screw 111 extends into a threaded bore 115 in the shaft part 11. The fixation is accomplished by means of the pressure that is exerted by the shaft head of the screw 111 onto the articulation part 105 toward the shaft, or by the pressing together of the contact faces between the rotating piece 33 and the shaft part 11.

The articulation shim 97 is embodied with a flat articulation face 43". This makes it possible to press the articulation shim and rotating piece together, causing deformation of material, whereby a very good hold can be achieved.

Thanks to the adjustability of the location of the spherical cap axis 81 relative to the directional axis 46, the cap 65 is displaceable, as indicated by the dotted line 109, relative to the humerus bone 86 or the outline of its cut face 103. On the one hand, this allows an approximate, rather than precise, implantation of the shaft part 11 into the bone 86 with respect to the desired location of the spherical cap 65, but also allows a displacement of the directional axis 46 upon the adjustment of the angle of the directional axis 46 to the shaft axis 15, or of the rotary position of the directional axis 46 relative to the humerus bone 86.

By the adjustment of the rotary position of the directional piece 41, in the third exemplary embodiment the location of the point where the directional axis 46 passes through the surface of the cut bone 103 also shifts. A rotation in the anterior direction causes a displacement of this passage point in the anterior direction. Conversely, a pivoting of the directional axis 46 in the cranial direction, that is, counterclockwise in terms of FIG. 7, causes a shift of the passage point of the directional axis through the cut plane 103 of the bone in the caudal direction, or in other words toward the bottom right in terms of FIG. 7.

Because a rotating piece 33, which is rotatable about a first axis 27 relative to the shaft part 11, is pivotably connected to the shaft part, and a directional piece 41 is disposed pivotably about a second axis 37 on this rotating piece 33, which second axis 37 is transverse to the first axis 27, an alignment of the directional piece relative to the cut plane 103 of the bone is possible in all directions. Resultant shifts in the passage point of the directional axis 46 through the cut plane 103 of the bone can be corrected in the same stroke with which the adjustment of the spherical cap axis 81 to the desired individual position with regard to the bone cut or the original cap location is done. As a result, all the necessary parameters can be adjusted, so that finally the spherical cap 65 can be placed at the optimal point corresponding to the original point.

The adjustment of the muscle tension is done, as in the conventional way, by the choice of one cap from a set of caps of different cap heights. However, it is also possible to set the definitive cap height by inserting a spacer shim 117 between the articulation shim 97 and the pressure shim 99. By using such spacer shims or pressure shims of different heights, which are easier to produce than spherical caps, it becomes unnecessary to produce and keep on hand complete sets of spherical caps of different cap heights. Also, because of the central disposition of the indentation 73 in the underside 79 of the cap 65, the possibility also exists of screwing the cap 65 with a thread onto the outer eccentric ring 64 or onto the oblong slot ring 87. This makes an infinitely variable adjustment of the cap height possible, but requires a fixation device, for instance in the form of a check nut that is screwed first onto the thread and that can be tightened against the underside 79 of the cap 65.

In summary, an endoprosthesis for a shoulder joint has a rotating piece 33, articulated to a shaft part 11 and rotatable about a first axis 27, and an axial directional piece 41 articulated to the rotating piece 33 about a second axis. The two pivot axes 27, 37 are transverse to one another, and the second axis 37 is transverse to the axis 46 of the directional piece 41. Either the spherical cap 65 is disposed directly on the directional piece 41, or an eccentric ring 63 or an oblong slot ring 87 that carries the spherical cap 65 is provided between the spherical cap 65 and the directional piece 41. Two or more eccentric rings 63, 64 are also possible. The spherical cap 65 can have a central or an eccentric conical face 73. The direction of the first axis 27 can be selected relatively freely, for instance parallel to the shaft axis 15, approximately parallel to the mean orientation of the directional axis 46, approximately parallel to the plane of the bone cut, and in particular also perpendicular to the directional axis 46 and to the second axis 37. It advantageously intersects the directional axis 46, for instance in the mean orientation thereof.

What is claimed is:

1. An endoprosthesis for a shoulder joint, comprising:
   a shaft part having an axial shaft stem for implantation into a humerus and having a shaft head;
   a rotating piece disposed on the shaft head, which rotating piece is rotatable relative to the shaft part about a first axis;
   at least one of an articulation face and a contact face between the shaft part and the rotating piece to provide for relative motion between the shaft part and the rotating piece about the first axis only;
   a directional piece extending along a directional axis and being supported rotatably relative to the rotating piece about a second axis, the second axis extending transversely to the first axis and transversely to the directional axis;
   at least one of an articulation face and a contact face between the rotating piece and the directional piece to provide for a relative motion between the rotating piece and the directional piece about the second axis only, the directional piece being pivotable in all directions relative to the shaft part;
   means for fixing the directional piece and the rotating piece relative to the shaft part in a selectable pivoted position; and
   a spherical cap connected to the shaft part via the directional piece.

2. The endoprosthesis of claim 1, comprising:
   at least one eccentric ring or oblong slot ring, independent of the directional piece, disposed between the directional piece and the spherical cap.

3. The endoprosthesis of claim 2, wherein the directional piece has an outer conical or cylindrical surface with a center of rotation about the directional axis, onto which conical or cylindrical surface the spherical cap, eccentric ring or oblong slot ring can be slipped.

4. The endoprosthesis of claim 1, wherein the direction of the first axis has a directional deviation from the direction of a neck axis of less than 60 degrees.

5. The endoprosthesis of claim 4, wherein the direction of the first axis is approximately parallel to a plane through the shaft axis and neck axis.

6. The endoprosthesis of claim 1, wherein the rotating piece, which is rotatable relative to the shaft part about the first axis, has a concave axial rotational body surface, oriented opposite to the directional piece, with the second axis as its center of rotation.

7. The endoprosthesis of claim 1, wherein the rotating piece, which is rotatable relative to the shaft part about the first axis, has a convex axial rotational body surface, oriented opposite to the directional piece, with the second axis as its center of rotation.

8. The endoprosthesis of claim 1, wherein the first axis intersects the second axis.

9. The endoprosthesis of claim 1, wherein the first axis and the second axis are spaced apart from one another.

10. The endoprosthesis of claim 1, wherein the first axis is transverse to a neck axis.

11. The endoprosthesis of claim 4, wherein the first axis is parallel to the neck axis.

12. The endoprosthesis of claim 1, wherein the first axis is oriented to either intersect or is oriented to coincide with a neck axis.

13. The endoprosthesis of claim 1, wherein rotary motions about the first axis and the second axis are individually fixable.

14. The endoprosthesis of claim 1, wherein rotary motions about the first axis and the second axis are fixable in common.

15. The endoprosthesis of claim 2, in which a single eccentric ring is used, wherein the spherical cap has an inner conical surface, which is disposed eccentrically relative to a spherical cap axis and which can be slipped onto an outer conical surface of the eccentric ring.

16. The endoprosthesis of claim 15, comprising:
   a manipulation head, which has an inner conical surface, disposed eccentrically relative to the spherical cap axis, which can be slipped onto the outer conical surface of the eccentric ring, and which manipulation head has an eccentricity equivalent to an eccentricity of the inner conical surface of the spherical cap, and which is shaped annularly in such a way that the eccentric ring is visible and adjustable through the annular opening of the manipulation head.

17. The endoprosthesis of claim 1, comprising:
   an oblong slot ring, which has an oblong slot with which it can be placed onto a connecting part of the directional piece, and having a fixation device, with which the oblong slot ring is fixable on the directional piece in an arbitrary displacement and rotational position relative to the directional piece.

18. The endoprosthesis of claim 17, wherein an indentation in the spherical cap, cooperating with the oblong slot ring, is disposed concentrically with the spherical cap axis.

19. The endoprosthesis of claim 1, comprising:
   a recess in the shaft part, with a side wall that corresponds to a face of rotation about the first axis, in which a rotating piece with an outline corresponding to the side wall is supported rotatably about the first axis, which rotating piece has an articulation face for the directional piece, in the form of a face of rotation about the second axis, and the directional piece has a complementary shape to this articulation face and an axial conical surface for slipping on an inner conical surface of the spherical cap or of an eccentric ring.

20. The endoprosthesis of claim 19, comprising:
   a threaded bore provided in the shaft part, the directional piece having an internal bore, in which there is space for the head of a screw; the rotating piece and the directional piece having a bore; and the directional piece being firmly screwed with the screw in the threaded bore, through the bores.

21. The endoprosthesis of claim 20, wherein the bore in the directional piece for a screw shaft is embodied as a slot, which allows a range of motion of the screw shaft of 30 degrees, and whose width is adapted to the diameter of the screw shaft.

22. The endoprosthesis of claim 1, wherein a radius of an articulation face of the directional piece is selected so that the directional piece, including the connecting part, is located inside a cylindrical segment having the radius.

23. The endoprosthesis of claim 7 wherein, in the rotating piece, a bore that is concentric with the articulation face about the second axis is provided; and a cylindrical body is disposed in the bore, which body is connected to a screw shaft, and a wall between the bore and the articulation face has a slot extending transversely to the second axis, through which slot the screw shaft passes; and the directional piece has an articulation shim and a pressure shim, and the articulation shim has a bore for the screw shaft and an articulation face corresponding to the articulation face of the rotating piece, and on an opposite side also has a pressure face cooperating with a pressure shim; and the pressure shim is connected to the screw shaft, and with a relative rotation between the screw shaft and the cylindrical body and/or the pressure shim, the distance between the cylindrical body and the pressure shim can be varied.

24. The endoprosthesis of claim 19, wherein the rotating piece is fixable on the shaft part with a ring that can be screwed onto or into the shaft part.

25. The endoprosthesis for a shoulder joint of claim 1, wherein at least two of the following parts are put together prior to implantation of the prosthesis and are available secured at least temporarily to one another: shaft part, rotating piece including an optional head piece, directional piece including an optional articulation shim and pressure shim, and screw, as well as an optional eccentric shim or oblong slot shim.

26. The endoprosthesis of claim 25, wherein at least one of two contact faces between the rotating piece and directional piece, between the rotating piece and the articulation shim, and between the directional piece and the screw anchored in the shaft part is shaped such that practically a linear contact exists between the contact faces.

27. The endoprosthesis of claim 26, wherein contact faces between the rotating piece and the directional piece, between the rotating piece and the articulation shim, and between the directional piece and the screw anchored in the shaft part correspond to one another in geometry and size.

28. The endoprosthesis of claim 4, wherein the directional deviation is less than 50 degrees.

29. The endoprothesis of claim 21, wherein the width of the slot is adapted to the diameter of a threadless part of the screw shaft that cooperates with the bore.

30. The endoprosthesis of claim 2, wherein the directional piece has an outer conical or cylindrical surface, whose center of rotation is the directional axis, onto which conical or cylindrical surface the spherical cap, eccentric ring or oblong slot ring can be slipped.

31. The endoprosthesis of claim 4, wherein the direction of the first axis has a directional deviation from the direction of a neck axis of less than 60 degrees.

32. The endoprosthesis of claim 1, wherein the at least one of an articulation face and a contact face between the shaft part and the rotating piece provide for relative motion between the shaft part and the rotating piece about only the first axis, and wherein the at least one of an articulation face and a contact face between the rotating piece and the directional piece provide for relative motion between the rotating piece and the directional piece about only the second axis.

33. The endoprosthesis of claim 32, wherein the direction of the first axis has a directional deviation from the direction of a neck axis of less than 60 degrees.

34. The endoprosthesis of claim 33, wherein the first axis is transverse to the neck axis.

35. The endoprosthesis of claim 1, wherein the shaft head constitutes a portion of the shaft part, wherein the shaft part is provided for implantation into the humerus.

36. The endoprosthesis of claim 1, wherein the shaft head constitutes a portion of the shaft part, wherein the shaft part is provided for implantation into the humerus.

37. The endoprosthesis of claim 1, comprising:
   means for fixing the directional piece in a selectable pivoted position relative to the shaft part;
   an oblong slot ring having an oblong slot with which the oblong slot ring is placed onto the directional piece; and
   a fixation device, with which the oblong slot ring is fixed on the directional piece in an arbitrary displacement and rotational position relative to the directional piece;
   wherein the oblong slot ring is disposed between the spherical cap and the directional piece.

38. The endoprosthesis for a shoulder joint of claim 37, wherein at least two of the following parts are put together prior to implantation of the prosthesis and are available secured at least temporarily to one another: shaft part, rotating piece including an optional head piece, directional piece including an optional articulation shim and pressure shim, and screw, as well as an optional eccentric shim or oblong slot shim.

39. The endoprosthesis of claim 38, wherein at least one of two contact faces between the rotating piece and directional piece, between the rotating piece and the articulation shim, and between the directional piece and the screw anchored in the shaft part is shaped such that practically a linear contact exists between the contact faces.

40. The endoprosthesis of claim 39, wherein contact faces between the rotating piece and the directional piece, between the rotating piece and the articulation shim, and between the directional piece and the screw anchored in the shaft part correspond to one another in geometry and size.

* * * * *